US012714803B1

(12) United States Patent
Guthikonda et al.

(10) Patent No.: US 12,714,803 B1
(45) Date of Patent: Aug. 25, 2026

(54) ARTERIAL LOCATION DEVICE AND METHOD FOR USE OF THE SAME

(71) Applicant: Mary Hitchcock Memorial Hospital, for itself and on behalf of Dartmouth-Hitchcock Clinic, Lebanon, NH (US)

(72) Inventors: Kiran Guthikonda, Grantham, NH (US); Ariel E. Attias, New York, NY (US); Julia Bellamy, New York, NY (US); Cameron Hasund, Severance, CO (US); Margaret J. Knox, Bethesda, MD (US); Sarah Lou, Los Angeles, CA (US); Scarlett Souter, Seabrook, NH (US)

(73) Assignee: Mary Hitchcock Memorial Hospital, for itself and on behalf of Dartmouth-Hitchcock Clinic, Lebanon, NH (US)

( * ) Notice: Subject to any disclaimer, the term of this patent is extended or adjusted under 35 U.S.C. 154(b) by 26 days.

(21) Appl. No.: 18/920,932

(22) Filed: Oct. 20, 2024

Related U.S. Application Data

(60) Provisional application No. 63/544,996, filed on Oct. 20, 2023.

(51) Int. Cl.
*A61M 5/42* (2006.01)
*A61B 8/00* (2006.01)
(Continued)

(52) U.S. Cl.
CPC ............... *A61M 5/427* (2013.01); *A61B 8/06* (2013.01); *A61B 8/461* (2013.01); *A61B 8/488* (2013.01);
(Continued)

(58) Field of Classification Search
CPC ........... A61M 5/427; A61B 8/06; A61B 8/488
See application file for complete search history.

(56) References Cited

U.S. PATENT DOCUMENTS 10,518,046 B2 12/2019 Wood
2007/0016050 A1 * 1/2007 Moehring ............. A61B 8/488 600/454

(Continued)

OTHER PUBLICATIONS

A better way to prepare for ultrasound exams. EPS Ultrasound. Published Aug. 22, 2018. Accessed Oct. 22, 2022. https://www.esp-inc.com/.

(Continued)

*Primary Examiner* — Rochelle D Turchen
(74) *Attorney, Agent, or Firm* — Loginov & Associates, PLLC; William A. Loginov

(57) ABSTRACT

This invention provides a location device for finding a peripheral artery having a Doppler ultrasound probe having a tip adapted to transmit and receive ultrasound signals with respect to a body. A processor receives ultrasound signals from the probe and processes the signals to recognize blood flow of the peripheral artery. The processor quantifies the recognized blood flow based upon signal strength. A housing is provided, which includes (a) a visual indicator, responsive to the processor, and that displays an indication when the signal strength exceeds a predetermined threshold, and (b) a pointer, located adjacent to the tip, that pinpoints a location on the body beneath which the peripheral artery is located. The indicator can be an array of LEDs proportional to signal strength and the pointer can be a laser.

20 Claims, 13 Drawing Sheets

(51) Int. Cl.
*A61B 8/06* (2006.01)
*A61M 25/01* (2006.01)

(52) U.S. Cl.
CPC . *A61M 25/0105* (2013.01); *A61B 2562/0219* (2013.01); *A61M 2025/0166* (2013.01); *A61M 2205/3375* (2013.01); *A61M 2205/584* (2013.01); *A61M 2205/587* (2013.01); *A61M 2230/06* (2013.01)

(56) References Cited

U.S. PATENT DOCUMENTS

2018/0015235 A1* 1/2018 Wood .................... A61M 5/427
2018/0132781 A1 5/2018 Weli-Numbere
2020/0268262 A1 8/2020 Melker
2023/0404528 A1* 12/2023 Fernando ............. A61B 8/4254

OTHER PUBLICATIONS

Arterial Line Placement. Saint Luke's Health System. Accessed Oct. 22, 2022. https://www.saintlukeskc.org/health-library/arterial-line-placement.

Begum, J. Clogged Arteries (Arterial Plaque). WebMD. Apr. 27, 2023. https://www.webmd.com/heart/picture-of-the-arteries.

Bloom J. Unlocking Common ED Procedures—Under Pressure: Arterial Lines in the Emergency Department. emDOCs. Published Nov. 21, 2019. Accessed Oct. 22, 2022. http://www.emdocs.net/unlocking-common-ed-procedures-under-pressure-arterial-lines-in-the-emergency-department/.

Brattain LJ, Pierce TT, Gjesteby LA, et al. AI-Enabled, Ultrasound-Guided Handheld Robotic Device for Femoral Vascular Access. Biosensors. 2021;11(12):522. doi:10.3390/bios11120522.

Cook JR, Bouchard RR, Emelianov SY. Tissue-mimicking phantoms for photoacoustic and ultrasonic imaging. Biomed Opt Express. 2011;2(11):3193-3206. doi:10.1364/BOE.2.003193.

Diffused 5mm LED Pack. Adafruit. Accessed Nov. 17, 2022.https://www.adafruit.com/product/4203.

Eisen LA, Minami T, Berger JS, Sekiguchi H, Mayo PH, Narasimhan M. Gender Disparity in Failure Rate for Arterial Catheter Attempts. J Intensive Care Med. 2007;22(3):166-172. doi:10.1177/0885066607299508.

Frédéric Michas. Hospitals in Europe—statistics and facts. Statista. Published Aug. 25, 2021. Accessed Nov. 17, 2022. https://www.statista.com/topics/8361/hospitals-in-europe/.

Getachew D, Astatkie A, Lemma K. Diameter, Vessel Thickness and Angle of Bifurcation of the Radial Artery in Ethiopian Cadavers. J Morphol Sci. 2018;35(02):129-135. doi:10.1055/s-0038-1669905.

Hartline R. Structures of Blood Vessels. In: Human Anatomy Labratory Manual. ; 2021. Accessed Oct. 21, 2022. https://bio.libretexts.org/Courses/West_Hills_College_-_Lemoore/Human_Anatomy_Laboratory_Manual_(Hartline)/18%3A_Cardiovascular_System_-_The_Blood_Vessels/18.02%3A_Structures_of_Bl ood_Vessels.

Helm EJ. Brief Overview of the Physics of Ultrasound. Presented at: 2016; University Hospitals Coventry and Warwickshire, UK.

Hooi FM, Kripfgans O, Carson PL. Acoustic attenuation imaging of tissue bulk properties with a priori information. J Acoust Soc Am. 2016; 140(3):2113-2122. doi:10.1121/1.4962983.

Jo G, Yang TH, Kim J, Koo JH, Kim YM. Development of a Mathematical Model for Age-Dependent Radial Artery Pulse Wave Analysis Based on Pulse Waveform Decomposition. IEEE Access. 2019;pp. 1-1. doi: 10.1109/ACCESS.2019.2962300.

Laser Diode 650nm 5mW 2.8V. Digi-Key Electronics. Accessed Nov. 17, 2022. https://www.digikey.com/en/products/detail/adafruit-industries-llc/1054/5629439.

Leipheimer JM, Balter ML, Chen AI, et al. First-in-human evaluation of a hand-held automated venipuncture device for rapid venous blood draws. Technology. 2020;07(03n04):98-107. doi:10.1142/S2339547819500067.

Limits of Resolution: The Rayleigh Criterion. In: Douglas College Physics 1207. ; 2018. Accessed Oct. 21, 2022. https://pressbooks.bccampus.ca/introductorygeneralphysics2phys1207/chapter/27-6-limits-of-resoluti on-the-rayleigh-criterion/.

Mankad, R. Coronary artery spasm: Cause for concern? Mayo Clinic. Published Aug. 26, 2022. Accessed Oct. 21, 2022. https://www.mayoclinic.org/diseases-conditions/angina/expert-answers/coronary-artery-spasm/faq-20058316.

Melniker LA, Leibner E, McKenney MG, Lopez P, Briggs WM, Mancuso CA. Randomized Controlled Clinical Trial of Point-of-Care, Limited Ultrasonography for Trauma in the Emergency Department: The First Sonography Outcomes Assessment Program Trial. Ann Emerg Med. 2006;48(3):227-235. doi:10.1016/j.annemergmed.2006.01.008.

Mengarelli M, Nepusz A, Kondrashova T. A Comparison of Point-of-Care Ultrasonography Use in Rural Versus Urban Emergency Departments Throughout Missouri. Mo Med. 2018;115(1):56-60.

Ogle S, et al. Arterial Line Placement. Vincent Lopez Rowe, ed. Published online Sep. 21, 2022. Accessed Oct. 21, 2022. https://emedicine.medscape.com/article/1999586-overview.

Paul Peter Urone. Ultrasound. In: College Physics. ; 2016. Accessed Nov. 17, 2022. https://jwu.pressbooks.pub/collegephysics/chapter/ultrasound/.

Physics of ultrasound. In: Clinical Echocardiography. Accessed Oct. 21, 2022. https://ecgwaves.com/topic/ultrasound-physics/.

Pierre L, Pasrija D, Keenaghan M. Arterial Lines. In: StatPearls Publishing; 2022. Accessed Oct. 21, 2022. http://www.ncbi.nlm.nih.gov/books/NBK499989/.

Point of care ultrasound at the bedside for Anesthesiology. Butterfly Network. Accessed Nov. 17, 2022. https://www.butterflynetwork.com/anesthesia-ultrasound.

Sam Zarbiv, Margaret Pisani. When Is a Peripheral Arterial Catheter (A-Line) Indicated in My ICU Patient? American College of Chest Physicians. Published Oct. 4, 2018. Accessed Oct. 22, 2022. https://www.chestnet.org/leadership/thought-leader-blog/2018/10/arterial-lines.

The Doppler Effect. The Physics Classroom. Accessed Oct. 22, 2022. https://www.physicsclassroom.com/class/waves/Lesson-3/The-Doppler-Effect.

The Medicare Payment Advisory Commission. Ambulatory Surgical Center Services.; 2021:60. Accessed Nov. 17, 2022. https://www.medpac.gov/wp-content/uploads/2021/10/mar21_medpac_report_ch5_sec.pdf.

Tissue Properties: Speed of Sound. IT'IS Foundation. Accessed Nov. 17, 2022. https://itis.swiss/virtual-population/tissue-properties/database/acoustic-properties/speed-of-sound/.

Ueda K. Ultrasound-Image Guided Versus Doppler Guided Versus Palpation Technique for Arterial Cannulation in Adults. clinicaltrials.gov; 2017. Accessed Oct. 20, 2022. https://clinicaltrials.gov/ct2/show/study/NCT01276171.

USB Audio Adapter. Adafruit. Accessed Nov. 17, 2022. https://www.adafruit.com/product/1475.

Weiner R, Ryan E, Yohannes-Tomicich J. Arterial Line Monitoring and Placement. In: Oropello JM, Pastores SM, Kvetan V, eds. Critical Care. McGraw-Hill Education; 2001. Accessed Oct. 21, 2022. accessanesthesiology.mhmedical.com/content.aspx?aid=1136419179.

Yeap YL, Wolfe JW, Stewart J, Backfish KM. Prospective Comparison of Ultrasound-Guided Versus Palpation Techniques for Arterial Line Placement by Residents in a Teaching Institution. J Grad Med Educ. 2019;11(2):177-181. Doi:10.4300/JGME-D-18-00592.1.

* cited by examiner

ARTERIAL LOCATION DEVICE AND METHOD FOR USE OF THE SAME

RELATED APPLICATION

This application claims the benefit of U.S. Provisional Application Ser. No. 63/544,996, entitled ARTERIAL LOCATION DEVICE AND METHOD FOR USE OF THE SAME, filed Oct. 20, 2023, the teachings of which are expressly incorporated herein by reference.

FIELD OF THE INVENTION

This invention relates to systems and methods for locating blood vessels, and application of intravascular catheters thereto.

BACKGROUND OF THE INVENTION

Arterial lines (also termed "A-lines") are peripheral vascular access catheters that are typically employed in the medical field to treat critically ill or surgical patients. A-lines are commonly used in intensive care medicine and anesthesia to monitor blood pressure directly and in real-time (rather than by intermittent and indirect measurement) and to obtain samples for arterial blood gas analysis. An A-line is typically inserted into the radial artery in the wrist, but can also be inserted into the brachial artery at the elbow, into the axillary artery in the axilla, into the femoral artery in the groin, into the *dorsalis* pedis artery in the foot, or into the ulnar artery in the wrist.

By way of background, FIG. 1 depicts a typical A-line arrangement 100 in which an exemplary patient 110 in which an A-line 120 is inserted to the (e.g.) radial artery at the patient's wrist/forearm 122. The exemplary A-line 120 is interconnected to the distal end of a saline-filled non-compressible tubing 124. In this exemplary arrangement, the opposing, proximal end of the tubing 124 is interconnected a pressure transducer assembly 130, that can also include (e.g.) a fluid flushing system 134 of known design. The pressure transducer 132 provides electrical signals/telemetry to a data-handling assembly and associated display 142 that provides desired graphical and/or alphanumeric information related to sensed conditions within the artery. The transducer assembly is in fluid communication with a pressure bag 150 containing saline in this embodiment. A pressure gauge 152 reports prevailing pressure in the bag 150, which is modulated 154 by an exemplary squeeze bulb 154 of known design. Note that the exemplary arrangement 100 is only one possible implementation and use for an A-line.

Typically, A-lines are inserted into an artery after such is located using using blind palpitation, ultrasound imaging or Doppler ultrasound techniques. Precise identification of the boundaries of patients' arteries at a location with sufficient blood flow can be challenging. This placement can be further complicated by other conditions, such as the thickness of tissue between the skin and artery, peripheral artery disease and/or calcification. Thus, healthcare professionals must often resort to multiple attempts to successfully cannulate the artery, and statistically, 26.8% of A-line insertions fail on the first insertion attempt, and approximately 20% fail after three attempts. In general, multiple/failed A-line placements can prove painful and potentially damaging to tissue, as well as resulting in additional complications, and delay of treatment. As such, repeated attempts to cannulate the artery with an A-line should be avoided if possible, and accurate first-time placement should be a goal.

While the above-described electronic devices can assist in placement of an A-line, they have disadvantages. For example, ultrasound imaging involves a relatively large unit and monitoring of a remote display screen while performing the insertion task, both of which present logistical and technical challenges to the user. Conversely, use of a hand-held Doppler probe can provide the general location of an artery, but is not tuned to such and cannot pinpoint its precise location under the skin to assist insertion.

As more than 8 million A-line placements occur in the U.S. each year, it is highly desirable to provide an improved, low-cost and accurate system for assisting in locating arteries for insertion of an A-line.

SUMMARY OF THE INVENTION

This invention overcomes disadvantages of the prior art by providing a device, system, and method for locating arteries for use (e.g.) in A-line placement that reduces the relatively high failure rate on first placement attempt. It comprises a probe arrangement that improves and supplements the artery detection capabilities of conventional Doppler ultrasound devices/probes. The artery location device of this invention provides an intuitive and informative visual output (display) to augment the subjective audio output provided in current Doppler probes. With the location device's additional information regarding the artery boundaries and blood flow, healthcare professionals (HCPs) can now more easily cannulate the (e.g.) radial artery of patients who may present challenges in cannulation, such as those with arterial complications. The location device includes a processing assembly having software and hardware that manipulate received Doppler ultrasound-based signals to detect artery location via blood flow patterns.

In an illustrative embodiment, a location device for finding a peripheral artery with respect to a body based upon ultrasound signals from a Doppler ultrasound probe having a tip adapted to transmit and receive the ultrasound signals is provided. A processor receives the ultrasound signals and processes the ultrasound signals to recognize blood flow of the peripheral artery. The processor quantifies the recognized blood flow based upon signal strength. A housing is provided, having (a) a visual indicator, responsive to the processor, that displays an indication when the signal strength exceeds a predetermined threshold, and (b) a pointer, positioned adjacent to the tip, that pinpoints a location on the body beneath which the peripheral artery is located. Illustratively, the pointer can comprises a structured light source, such as a laser, projecting a beam. The housing can include an accelerometer interconnected with the processor, and the processor can be adapted to provide a signal relative to at least one of the indicator and the pointer when movement sensed by the accelerometer exceeds a predetermined threshold. The pointer can be adapted to deactivate when movement sensed by the accelerometer exceeds the predetermined threshold. Additionally, the pointer and/or the indicator can be located on an arm overlying an elongated main body of the housing. The indicator can comprise an array of a plurality of light sources located on the arm, and each of the light sources can be constructed and arranged to illuminate based upon the signal strength. The light sources can each be LEDs all having the same illumination color, or at least one of the LEDs can have a differing illumination color from others of the LEDs so as to define differing threshold conditions The beam can be activated based when the signal strength exceeds a predetermined threshold. The indicator can comprise a display screen constructed and arranged to display information relative to the signal strength. The ultrasound signals can be passed through a bandpass filter, audio transformer and analog-to-digital converter. The ultrasound signals can be passed through a bandpass filter, audio transformer and analog-to-digital converter. The processor can be constructed and arranged to identify heartbeat characteristics from filtered and digitized versions of the ultrasound signals and measure an intensity thereof.

In an illustrative embodiment, a method for locating the peripheral artery by moving the location device with respect to a region of interest on the body of the patient, based at least upon information given to the user by the indicator, is provided. The method can include inserting an A-line catheter into the peripheral artery at the pinpointed location. Illustratively, a structured light beam is projected with the pointer, and data can be received from an accelerometer, whereby a signal relative to at least one of the indicator and the pointer is provided when movement sensed by the accelerometer exceeds a predetermined threshold. The pointer can be deactivated when movement sensed by the accelerometer exceeds the predetermined threshold. The indicator can comprise a display screen constructed and arranged to display information relative to the signal strength. Illustratively, the ultrasound signals can be passed through a bandpass filter, audio transformer and analog-to-digital converter. Heartbeat characteristics can be identified from filtered and digitized versions of the ultrasound signals, and an intensity thereof can be measured accordingly.

BRIEF DESCRIPTION OF THE DRAWINGS

The invention description below refers to the accompanying drawings, of which.

DETAILED DESCRIPTION

I. System Overview

Figure 1:
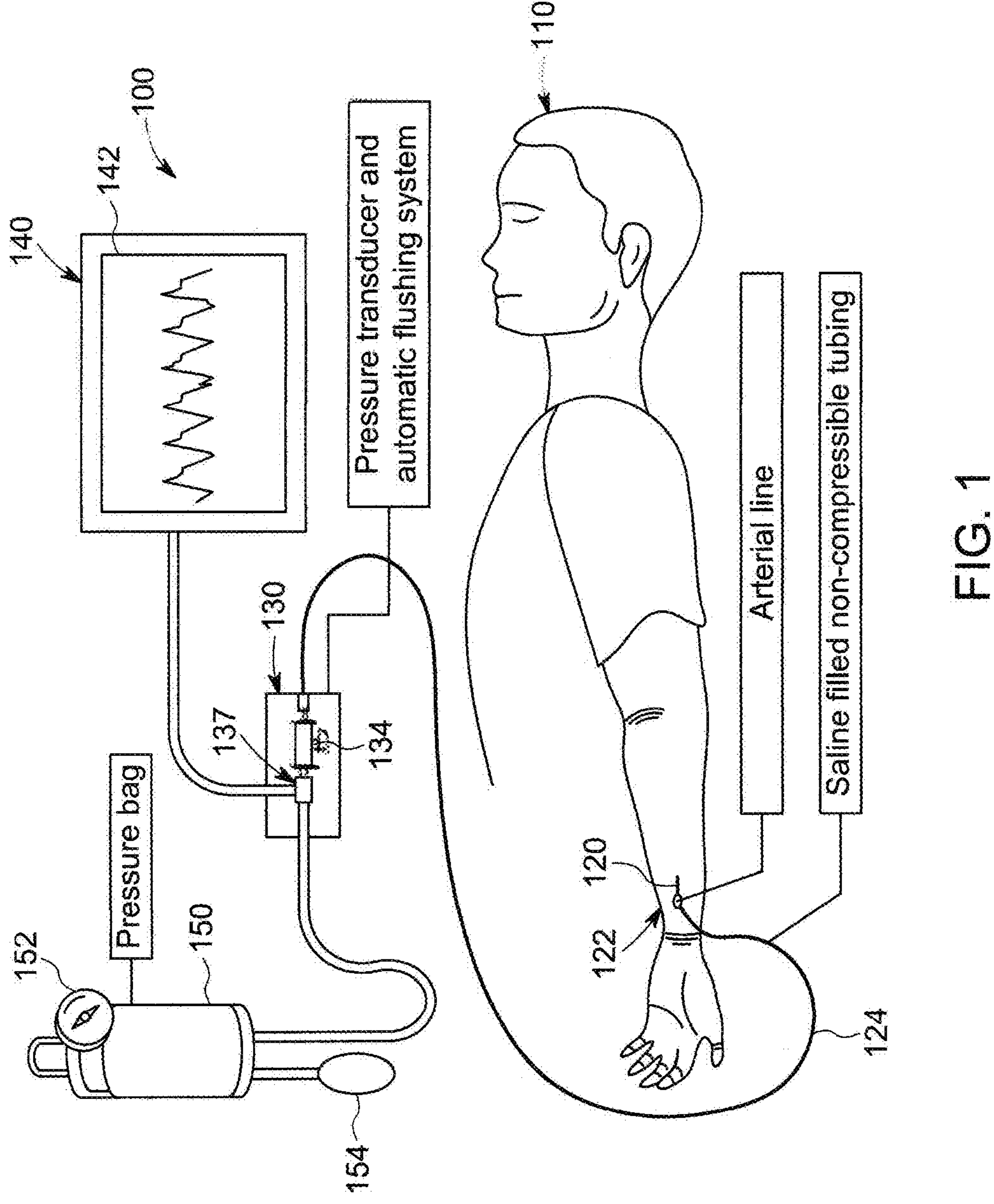
FIG. 1 is a diagram showing an exemplary A-line placement in the wrist/forearm of a patient.
Figure 2:
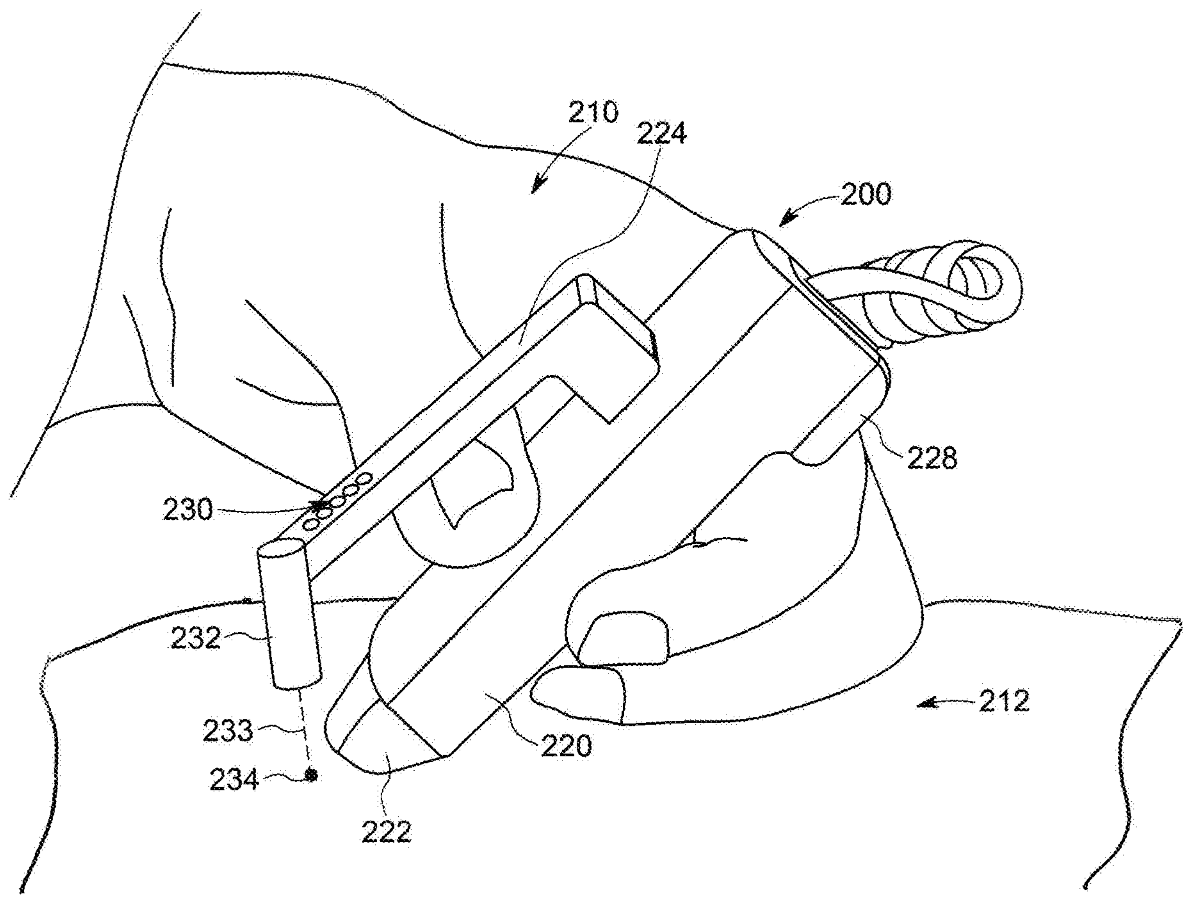
FIG. 2 is a perspective view of an artery location device according to an illustrative embodiment, shown in operation.

Reference is made to FIG. 2, which shows an artery location device 200 that is shown manipulated by a user's hand 210, with respect to the surface 212 of a patient's body part (e.g. a forearm). The user is searching for the location of an artery beneath the skin for placement of an A-line. As shown, the location device 200 defines a generalized housing shape (described in more detail in FIG. 2A, below), which includes an elongate housing main body 220 with a Doppler ultrasound probe (also termed "transducer") 222, typically, of conventional design at its distal end. The user angles the device as shown to place the transceiver into contact with the forearm surface 212. The main body 220 includes various electronics, described below, that allow for self-contained processing of received Doppler signals to generate appropriate visual and auditory feedback for the user as to pinpointed location of an artery. In an embodiment, the housing can be a case that overlies an existing, commercially available Doppler probe structure with the distal tip thereof remaining exposed. Alternatively, in a standalone version the entire housing can be purpose-built to enclose electronics and a Doppler ultrasound transceiver as described below.

The housing 220 (in this example) also carries a formation or structure 228 containing a motion sensing device—for example a solid-state accelerometer of conventional design. The motion sensor transmits motion vector information to the device processor as described generally below.

In this example, the housing includes an overlying arm 224 that provides an array 230 of (e.g.) discrete light sources, for example, LEDs, in one or more colors. By way of non-limiting example, the LED array can consist of a combination of red, yellow and green LEDs. The processing circuitry of that device 200 communicates with the array 230 to selectively activate LEDs in sequence so that the stronger the signal indicating an artery, the larger the number of LEDs are illuminated. In one non-limiting example, all LEDs can be the same color (e.g. green) and the number of illuminated LEDs in succession is proportional to the strength of the signal in detecting localization/proximity of an artery. In another operational example, the strongest signal can be indicated by one or more adjacent green LEDs, while a weaker signal is indicated by yellow LEDs and no signal is indicated by a red LED, or no illumination.

The overlying arm 224 also includes a pointing mechanism/assembly 232—for example a collimated laser beam 233—that projects a dot or other structured light shape onto the detected artery region slightly ahead of the Doppler transceiver 222 and in line with the detected, underlying artery location. This projected dot 234 indicates the area into which the A-line can be inserted by the user. Thus, while the user views the LED array for an indication of a strongest signal, the pointer guides the user to the specific location of the signal.

Figure 3:
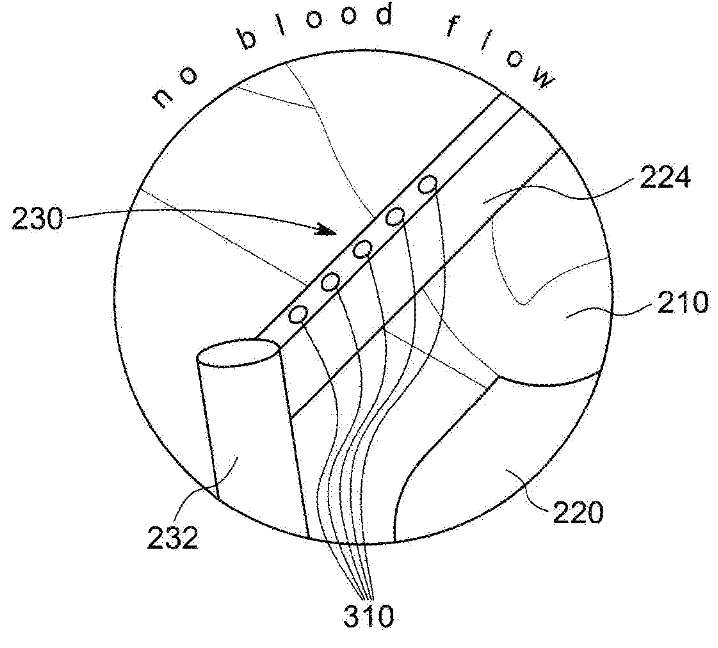
FIG. 3 is a fragmentary perspective view of the location device of FIG. 2, showing an indicator light array in which no blood flow and/or no localized artery is detected.
Figure 4:
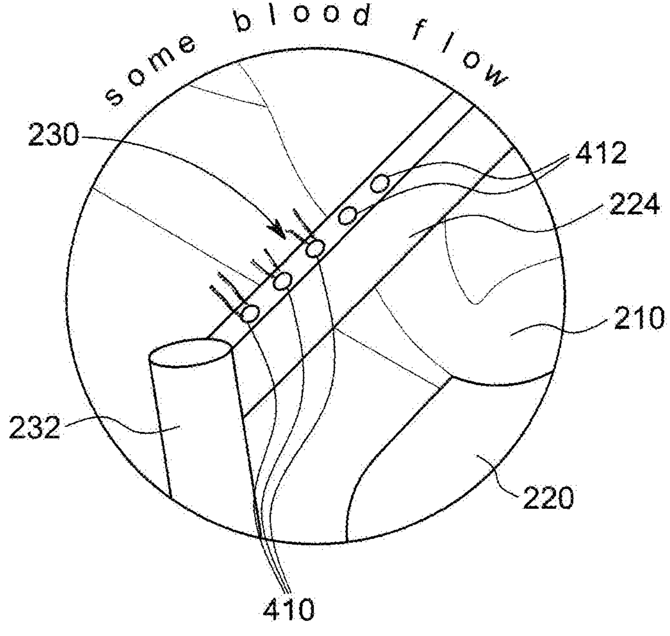
FIG. 4 is a fragmentary perspective view of the location device of FIG. 2, showing the indicator light array in which some blood flow and/or a partially localized artery is detected.
Figure 5:
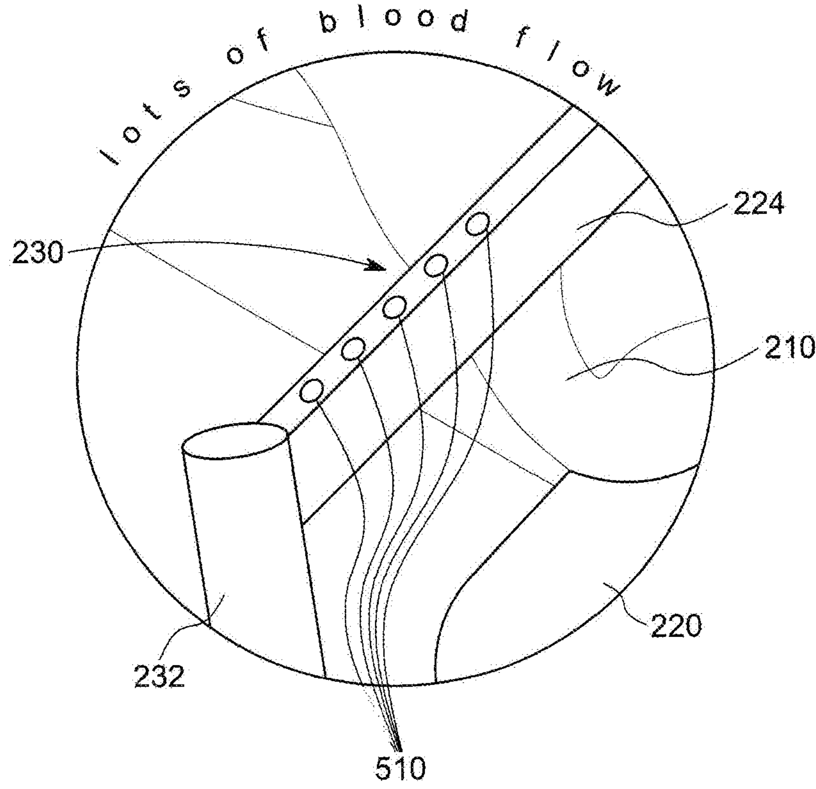
FIG. 5 is a fragmentary perspective view of the location device of FIG. 2, showing an indicator light array in which maximal blood flow and/or a fully localized artery is detected.

By way of operational example, FIG. 3 shows a positioning of the device in which no significant blood flow from an underlying artery is detected by the Doppler probe. As such none of the individual LEDs 310 on the arm 224 are illuminated. In FIG. 4, the probe is moved to a region on the patient that detects some blood flow from an underlying artery, and thus, a subset of the overall array 230 of LEDs 410 is illuminated and another subset of LEDs remains unlit. In FIG. 5, the probe substantially overlies a candidate artery and senses significant blood flow. Thus, all LEDs 510 in the array 230 are illuminated. An audible alarm can also be issued to alert the user in addition to any preexisting sound produced by the functioning Doppler probe. The pointer dot (234 in FIG. 2) is used to guide insertion of the catheter tip at this location.

Figure 2A:
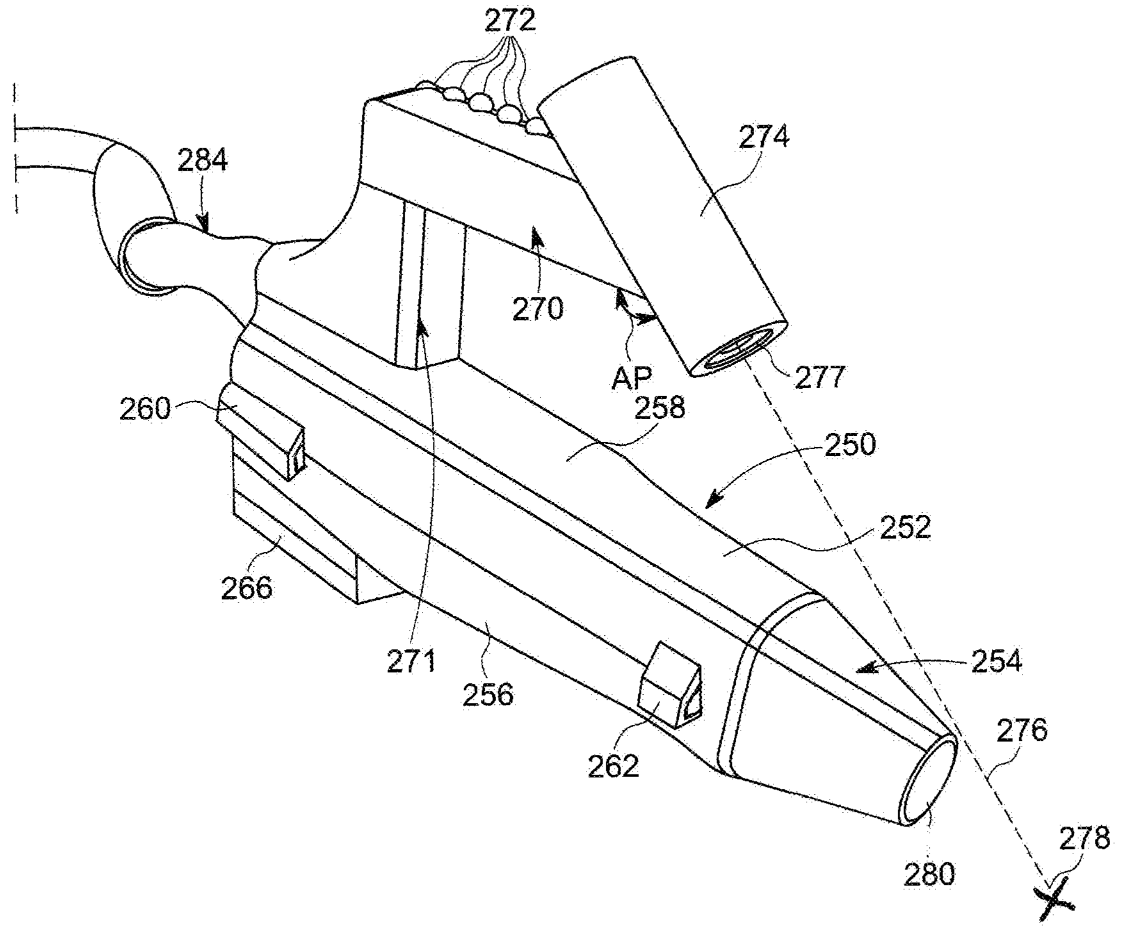
FIG. 2A is a more detailed perspective view of the location device of FIG. 2, showing details of an illustrative housing structure.

With further reference to FIG. 2A a version 250 of the location device, which includes an integrally molded housing 252, is shown. This version is functionally similar to that of FIG. 2 and other illustrations herein. The housing can be constructed from a polymer (e.g. ABS, PET, nylon, etc.) that is acceptable for use in medical instruments employed in non-invasive scenarios. As shown, the exemplary housing 252 that encloses the Doppler ultrasound probe 254 of (e.g.) conventional, or customized, design and function. The main body of the housing 252 is adapted for grasping and generally defines an elongate, somewhat rectangular cross-sectional shape similar to a conventional probe. In this embodiment, the housing defines a lower half 256 and upper half 258. The halves can be joined by unitarily molded clips 260 and 262, formed on the upper half 258, and removably engaging appropriately sized/shaped protrusions (not shown) on the lower half 256. The lower half 256 includes a proximal, bottom-oriented protrusion 266 that houses an accelerometer, or another type motion sensing device that provides motion vector data to the system processor. The upper half 258 includes a unitarily molded/formed or integrally attached arm 270. The arm 270 includes a riser 271 that elevates it so as to overlie the main body, like that of the embodiment in FIG. 2. The arm 270 includes a plurality of top-mounted light sources (LEDs) 272 in a linear array that indicate proximity to an underlying artery as described above. The distal end of the arm includes a housing 274 for a (e.g.) laser pointer or similar structured light source 277 that projects a beam (dashed line 276) that forms a dot (X mark 278) ahead of the distalmost end 280 of the probe 254. The housing 274 and pointer beam source axis are oriented at a non-perpendicular angle AP relative to the direction of extension of the arm 270 (which is parallel to the elongation direction of the main body), so that the beam is free of interference/obstruction by the probe 254 and accurately indicates the location of the artery to be detected. That is, the arm 270 is shorter than the main body and the angle AP compensates for this shortfall. In this embodiment, the arm and the main body include proximal cabling 284 that provide power and (optionally) data to a base power supply and/or processing assembly. In various embodiments, the entire unit can be self-contained with on-board (e.g. rechargeable) power, electronics and processing components.

As described below the structured light beam pointer 277, as well as the indicator array 272, are only one of a variety of possible pointing and indicating arrangements that can be employed with the Doppler probe of this invention.

II. Functional Components and Processor

Figure 6:
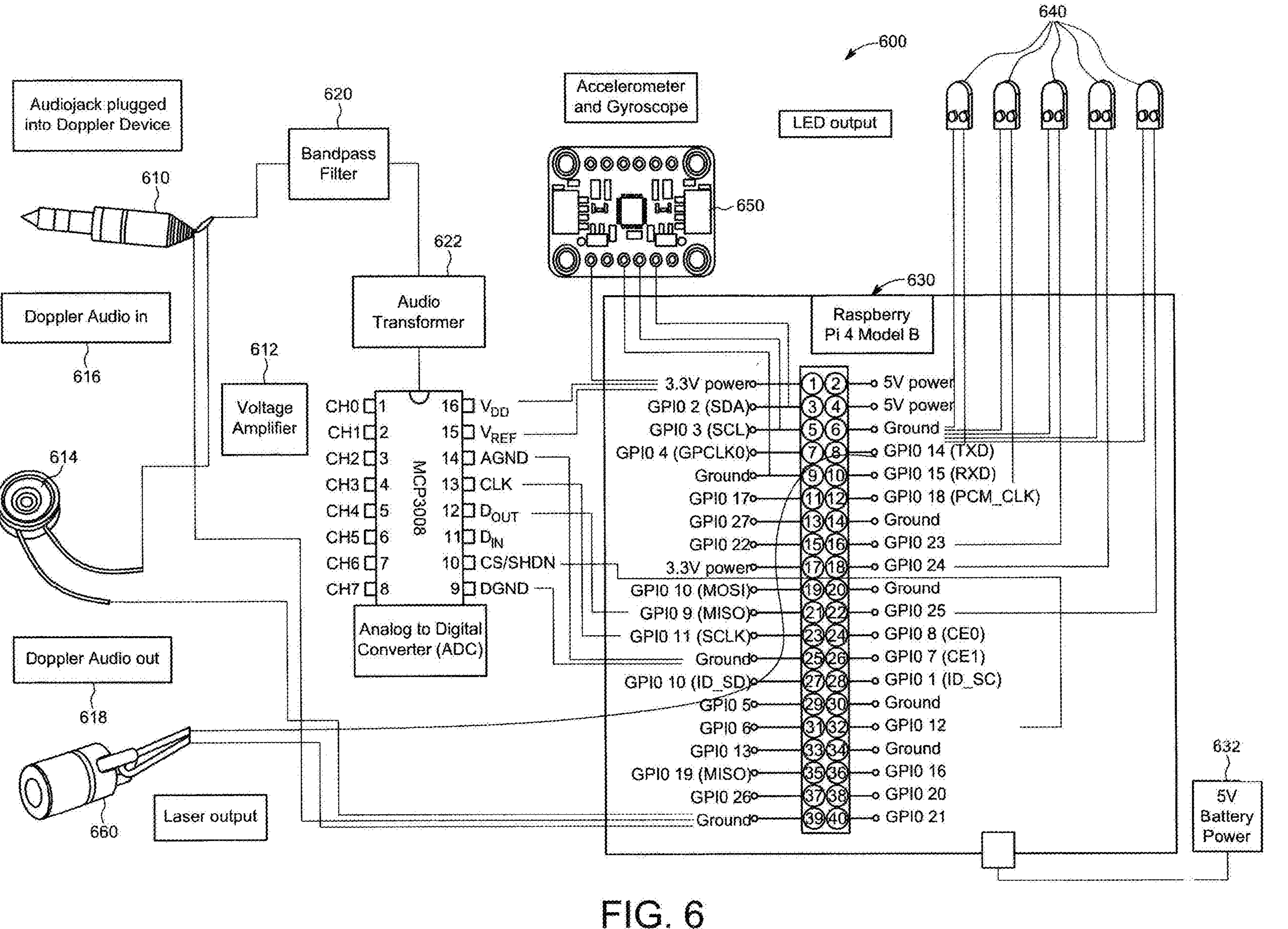
FIG. 6 is a diagram of the arrangement of electronic components that can be employed to implement the functions of the location device of FIG. 2.

Reference is now made to FIG. 6, which shows a generalized circuit diagram 600 and associated functional components for a basic location device, such as that shown in FIG. 2. Note that this example represents an experimental implementation of the device, and that a commercially available version would include direct interconnections and purpose-built processing circuitry—for example, ASICs and/or FPGAs. As shown, the circuit/component arrangement 600 includes a jack or other connector 610 that interconnects to the audio-in connection of a conventional Doppler probe. More particularly, the Doppler audio component 614 is interconnected with the jack 610 via a voltage amplifier 612. The jack 610 also interconnects to a bandpass filter 620 and audio transformer 622, which is connected to an analog-to-digital converter (ADC) 626 of appropriate design. The component generates a Doppler audio-in signal 616 a Doppler audio out signal 618. The ADC 626 is interconnected with power, ground and a microprocessor (e.g. (Raspberry Pi 4 Model B computer processing platform 630 via (e.g.) GPIO 12). The exemplary Raspberry Pi computing device, commercially available through Raspberry Pi, Ltd of Cambridge, United Kingdom, is a small scale, robust computer capable of executing software in the form of non-transitory computer-readable program instructions. The I/O pinouts send and receive digital signals based upon the applicable software instructions. Instead of a microprocessor, an integrated circuit may be designed for this same function. These allow for handling of the Doppler signal in digitized form and output of various information, such as driving of the above-described signal strength LEDs 640. As shown, each LED is connected to ground and a discrete GPIO (e.g. GPIO 14, 18, 23, 24 and 25, respectively), which is/are individually addressed by the program. The computer processing platform/Raspberry Pi is connected to a 5V (e.g. battery) power source 632.

The processing platform 630 is also connected to a solid state accelerometer and gyroscope unit 650, which can be a commercially available component. As shown, it is connected to power and ground, and data is output to discrete I/O pinouts (e.g. GPIO 2 and 3). The accelerometer and gyroscope provide motion sensing data—typically in the form of acceleration and direction-based vectors. This information can be used to track the motion of the location device as it passes along the patient's skin, and determine if its tilt and general orientation is acceptable to provide the proper localization of the laser pointer dot. That is, if the device becomes tilted, the point of insertion may miss the artery. Improper tilt can be indicated by the LED display. For safety purposes, the laser can be automatically shut off if the acceleration of the device as measured by the accelerometer exceeds a threshold value.

The pointing assembly, in the form of a collimated laser diode unit 660 is shown connected to the pinout (e.g. GPIO 14) for one of the LEDs 640. In operation, this can be the first LED illuminated in the array so that the pointer only activates upon the presence of some blood flow.

Note that the timeframe for activation of discrete indicator LEDs and the laser pointer should be selected to provide a consistent display without jumpiness, while also affording an accurate indication of current blood flow state received from the Doppler probe. These is some inherent lag between sensing and motion of the device, and selection of a time frame for sampling data helps to address such.

III. Blood Flow Signal Handling

Figure 7:
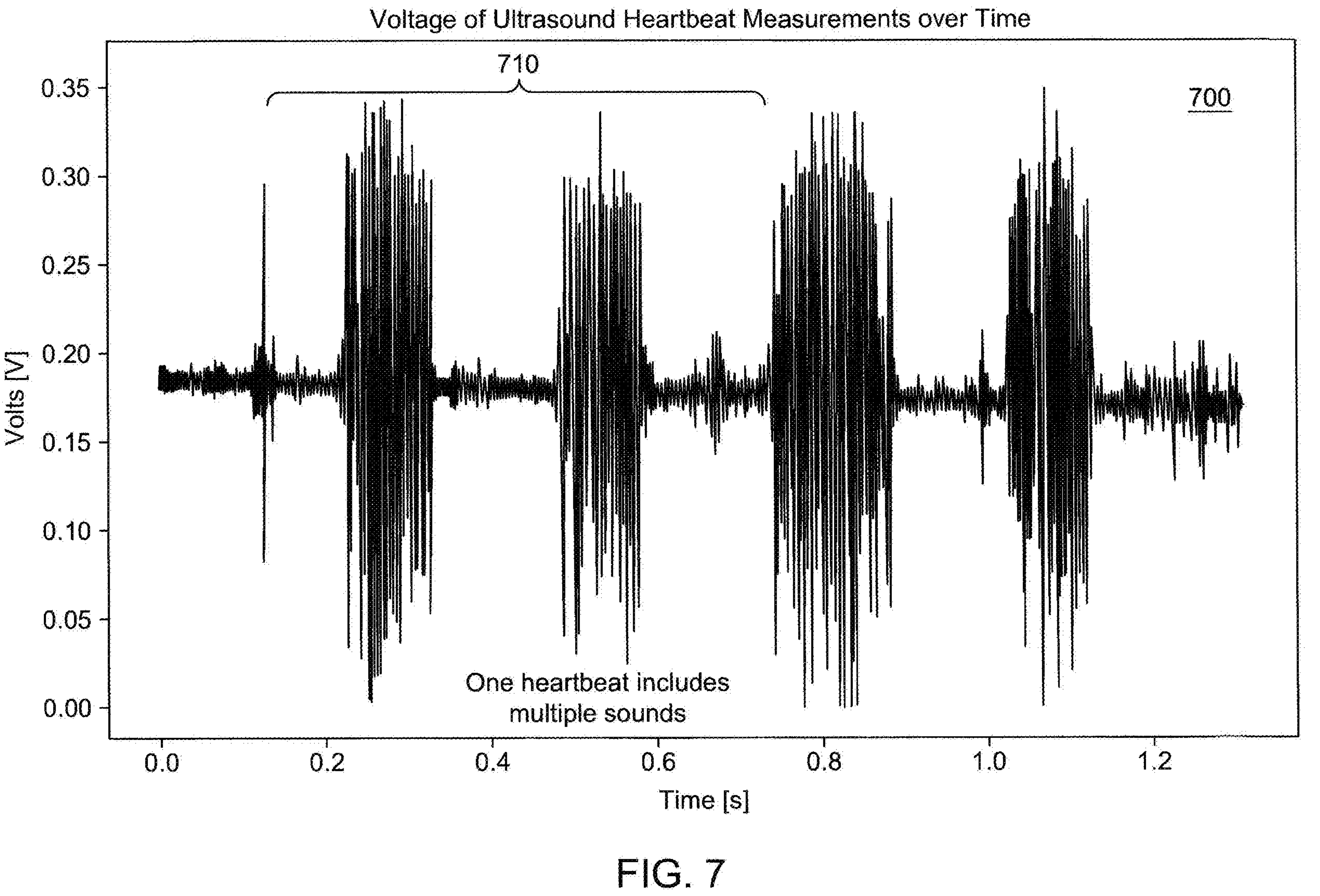
FIG. 7 is a graph showing an exemplary voltage output of an ultrasound probe detecting an exemplary heartbeat, which is used for modelling artery detection in the circuitry of FIG. 6.
Figure 8:
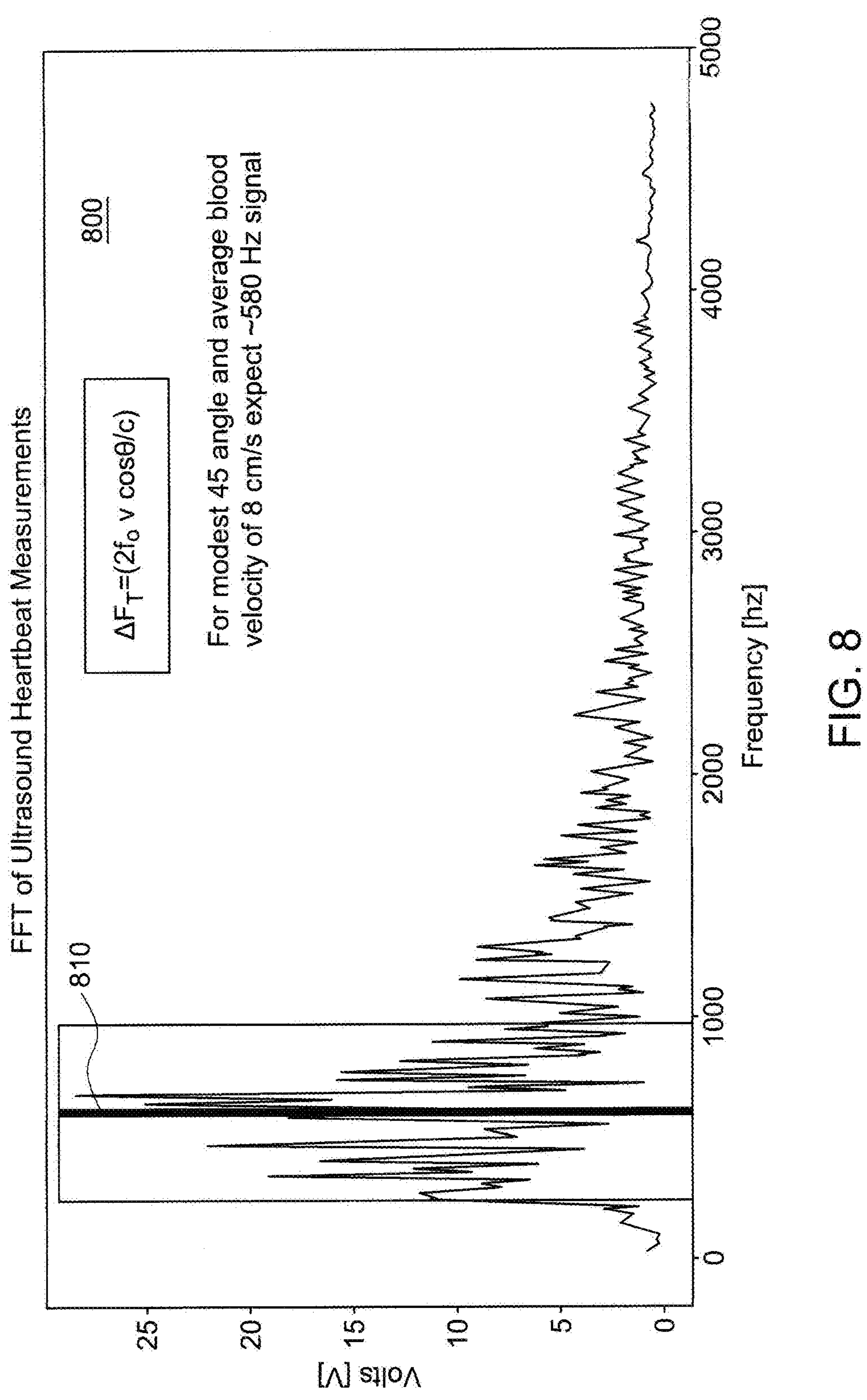
FIG. 8 is a graph showing a Fast Fourier Transform (FFT) analysis of ultrasound heartbeat measurements in accordance with FIG. 7.

FIG. 7 shows a graph 700 of an exemplary heartbeat signal determined by ultrasound sensing. As shown, an exemplary heartbeat 710 contains multiple sounds that define a recognizable pattern. The heartbeat 710 can be translated into an FFT graph 800 in the frequency domain as shown in FIG. 8. As noted, for a probe angle of approximately 45 degrees and approximate velocity of blood through an artery of 8 cm/s, the signal 810 can be characterized by a peak around 580 Hz. The processing platform can be programmed to search for peaks in the received signal and then operate on such peaks to localize arterial blood flow by pinpointing a maximum intensity (i.e. output voltage) for the signal. This can also be functionalized as additional hardware components to the band pass filter 620.

Figure 9:
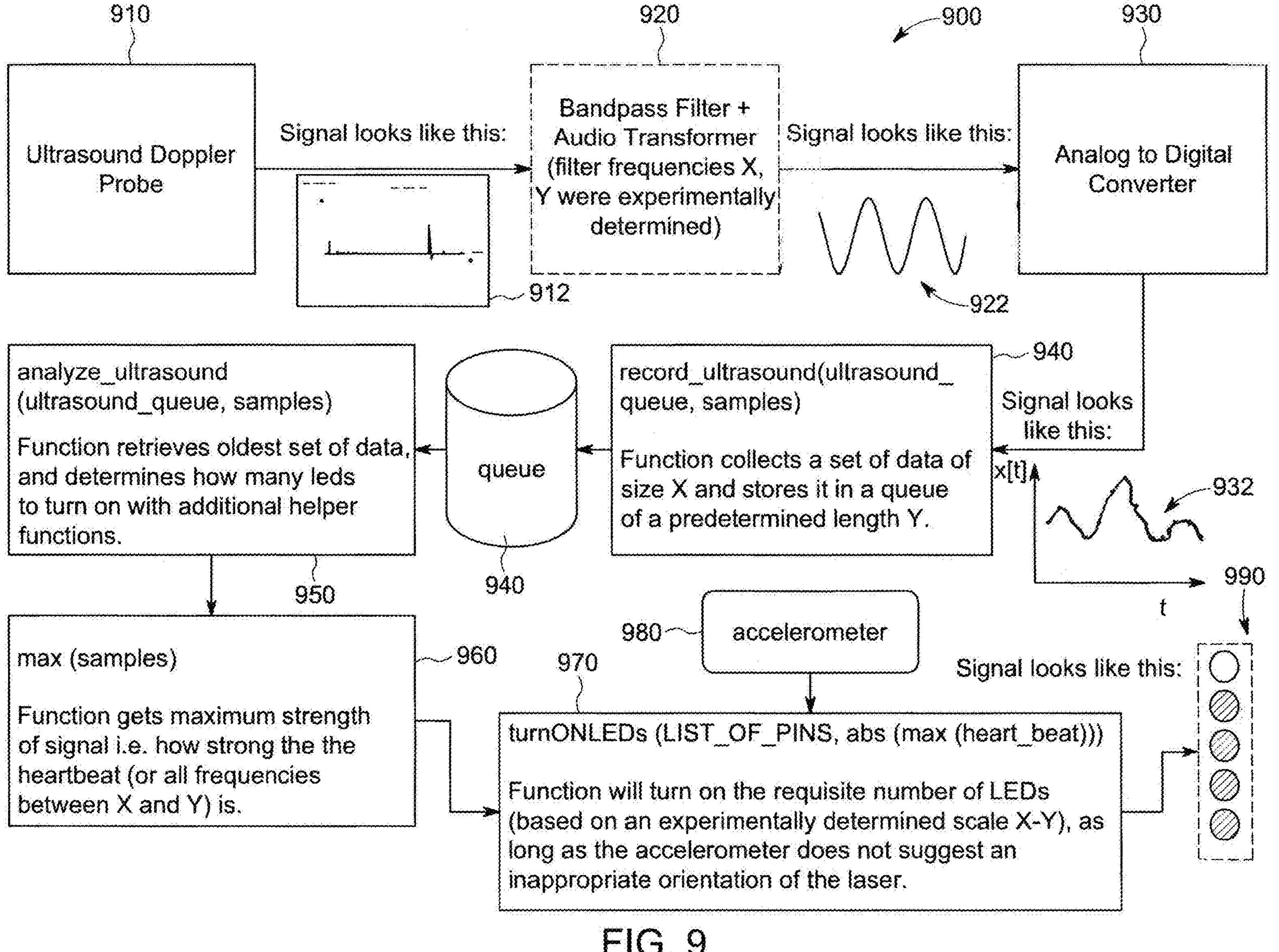
FIG. 9 is a flow diagram showing the runtime procedure performed by the processing arrangement in receiving ultrasound signals and displaying results for the location device of FIG. 2.

FIG. 9 show a flow diagram of a generalized procedure for signal receipt and handing according to an exemplary embodiment. Note that various functions/steps include fragments of code used in programming the processing platform by way of non-limiting example. The Doppler probe 910 generates a signal of sensed arterial blood flow that is characterized by a certain maximum voltage/amplitude. The signal 912 is then passed through the above-described bandpass filter and audio transformer 920, in which the X and Y values of filter frequencies are determined through trial and error experimentation based upon comparative measurements versus known artery locations. Notably, these components help to minimize complexity in the process software. The resulting signal defines a sinusoidal curve 922 as shown. This signal 922 is then routed through the above-described ADC 930. The signal is translated into a time-based (t) set 932 of values x(t). These values are processed by a function that collects a set of data of size X and stores it in a queue 940 of a predetermined length Y. The queue 940 is then passed to a function 950, which retrieves the oldest set of data and determines how many LEDs (or other indicating modality) to activate. Additional helper functions can be used in this step of the procedure. Next, a function 960 obtains the maximum signal strength by determining maximum strength of the sampled heartbeat signal between X and Y. This result of the function 960 is passed to the indicator function 970 that activates the number of LEDs (or other indicator modality) in proportion to the read maximum strength of the signal at the current time. The indication is based upon a linear (or other) proportionality function in which upper and lower limits for activating each LED (in array 990) are determined by (e.g.) trial and error experimentation based upon measurements of a known artery. The function 970 also incorporates an accelerometer 980 that monitors motion on a continuous basis. The process determines if device motion exceeds a predetermined threshold or otherwise indicates an inappropriate tilt that may cause the laser to miss the artery. In operation, the system establishes an accepted orientation based upon various internal and external factors and monitors for maintenance of this orientation during motion. In general, the accelerometer affords a further margin of safety in use of the device and can deactivate one or more LEDs 990 to indicate inappropriate tilt.

IV. Operation

Figure 10:
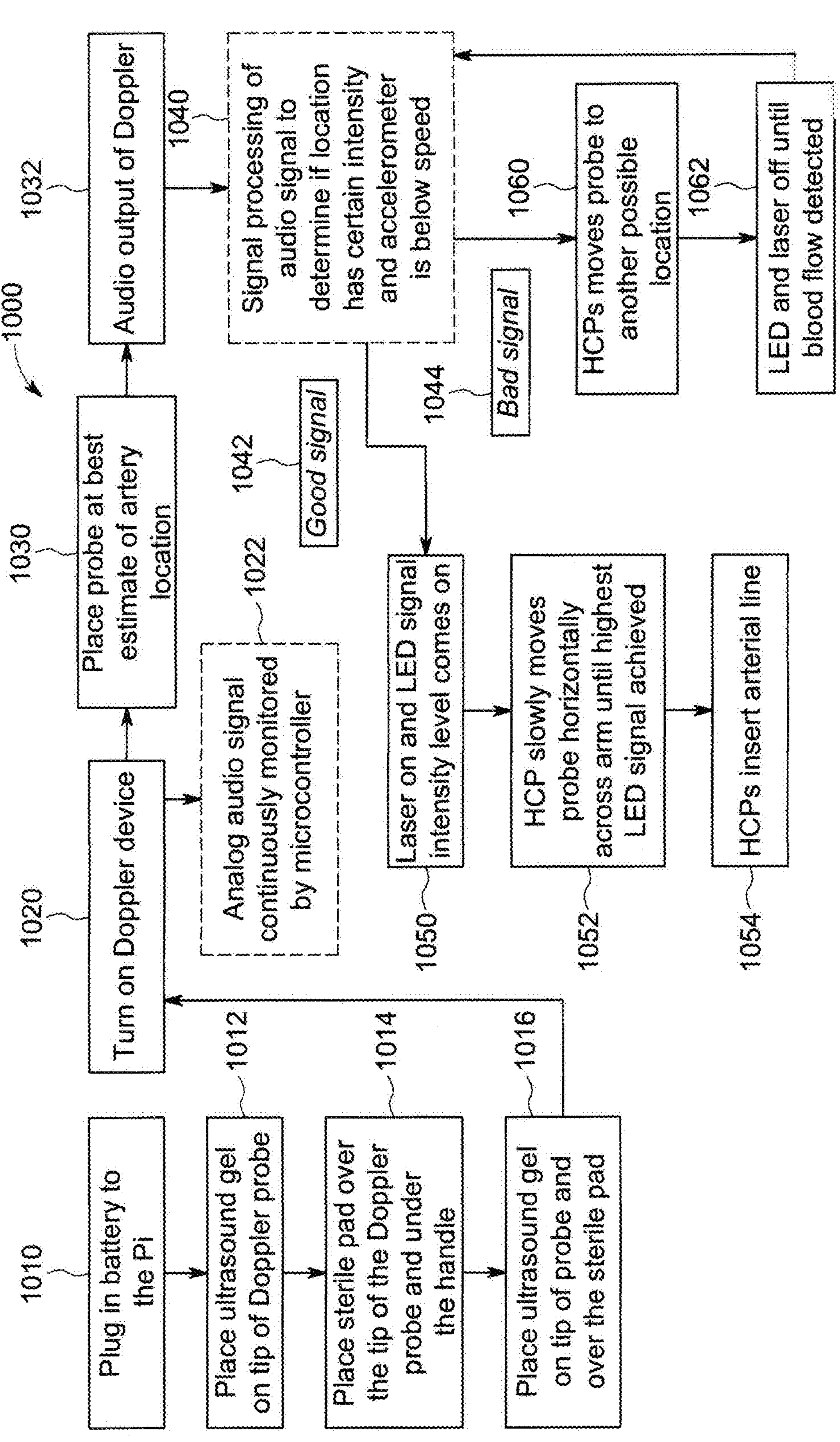
FIG. 10 is a flow diagram showing an overall procedure for operation and use of the location device of FIG. 2.

Reference is made to FIG. 10, which shows an overall operational procedure 1000. The location device is initially powered to activate to (e.g.) on-board processor in step 1010. Ultrasound gel is then applied by a practitioner (HCP) to a patient's arm or other extremity in the region of the target artery in step 1012. A sterile pad can then be placed over the tip of the Doppler probe and generally cover areas that may contact the patient is step 1014. Further gel can be placed over the tip of the probe and sterile pad in step 1016. The Doppler device is activated in step 1020 (which can occur as part of general power up in (e.g.) step 1010). The processing platform then continuously monitors the analog audio signal (step 1022). In decision step 1040, the resulting audio output of the Doppler probe (block 1032), in digital form, is used by the processing platform to determine if the sensed location on the patient has a predetermined intensity characteristic of blood flow and the accelerometer has not sensed a motion in excess of a threshold.

If a good signal is received (block 1042), based upon measurement of at least some arterial blood flow, then the processor activates the laser and illuminates one or more indicator LEDs (depending on intensity). Based upon the indicator level, the as the device is slowly moved by the HCP about the patent's area of interest until the LED indicators show the highest detected signal (step 1052). The probe is held at that point while the laser or other pointing device marks the spot for insertion of the A-line. The HCP then inserts the A-line at this marked location (step 1054).

If a bad signal is received (block 1044), based upon lack of detected blood flow, or a minimal detection below a threshold, the LED indicators and laser remain deactivated (step 1062), while the HCP attempts to move the device to another candidate location in the patient's region of interest (step 1060). The signal processing function/step 1040 continues to analyze the digitized Doppler audio output until sufficient blood flow is detected, and then issues a good signal (1042) indication via activation of appropriate LEDs and the pointer laser (step 1050).

V. Alternate Embodiments

It is expressly contemplated that the above-described design can be modified to provide alternate implementations of the blood flow indicator, pointer assembly, or both. In various embodiments, a commercially available Doppler ultrasound probe can be encased in a housing (e.g. that shown in FIG. 2A), and the functionalities of the location device herein can be provided as optional features in the housing.

Figure 11:
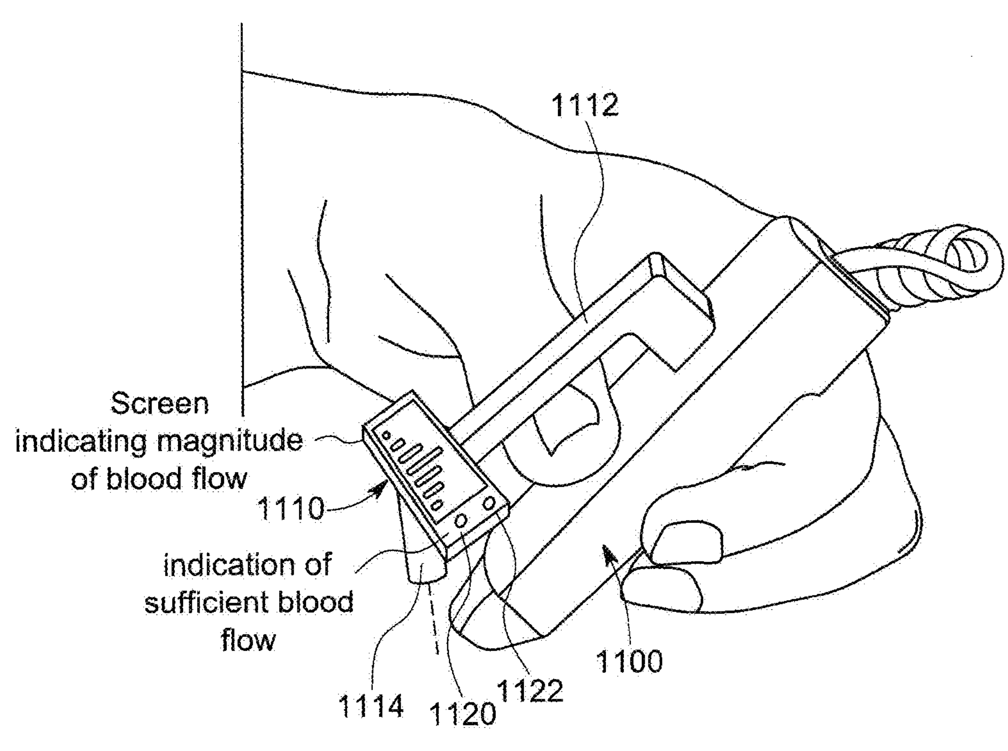
FIG. 11 is a perspective view of an artery location device having an integral display screen for depict magnitude of blood flow according to an alternate embodiment.

As shown in FIG. 11, the artery location device 1100 includes a display screen (for example a conventional LCD display) 1110 mounted on the end of the overlying arm 1112 adjacent to the pointer 1114. The LCD board can include indicator (e.g. LEDs) 1120 and 1122. The LEDs 1120 and 1122 can each be a different color, or multi-color. A red LED can indicate no or insufficient blood flow while a green LED can indicate sufficient blood blow. The LCD display 1110 can provide a variety of graphical and/or alphanumeric information to the user. As shown, the display can define a set of bars that guide centering of the device over the artery—that is, when the highest bar is centered, the device and laser spot are centered. Other indications can be included, for example, the bars flashing, turning green and/or another color, etc.

Figure 12:
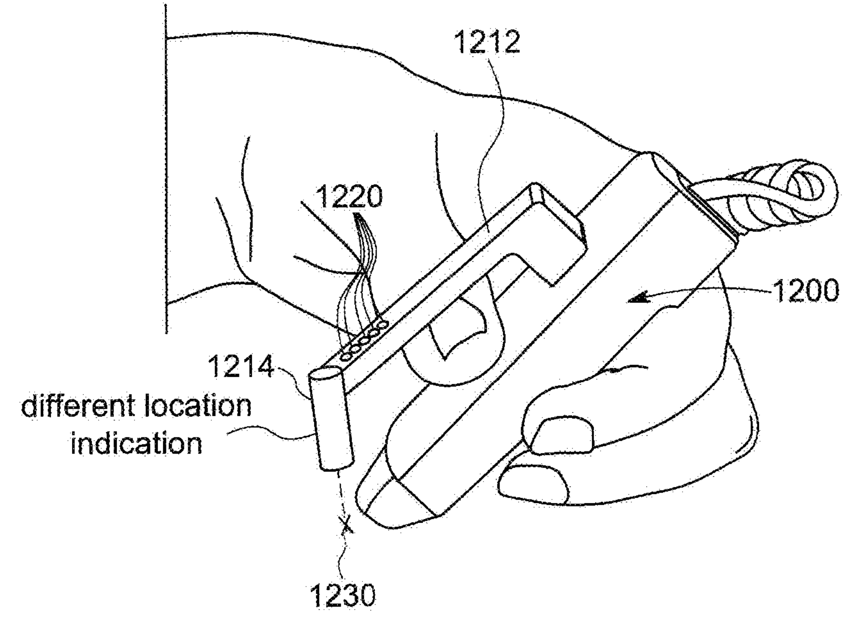
FIG. 12 is a perspective view of an artery location device having a location pointer that uses structured light (e.g. a cross) to indicate artery location according to an alternate embodiment.

With reference now to FIG. 12, an alternate implementation of the artery location device 1200 includes an overlying arm 1212 with a distal laser pointer 1214 and indicator (e.g.) LEDs. The structured light pattern projected by the laser 1214 in this exemplary embodiment can define a different pattern than a basic dot—for example a cruciform shape 1230. A variety of commercially available filters/ lenses can be employed to create desired patterns for assisting the HCP in localizing the insertion site. For example, a reticle, concentric circles, etc.

Figure 13:
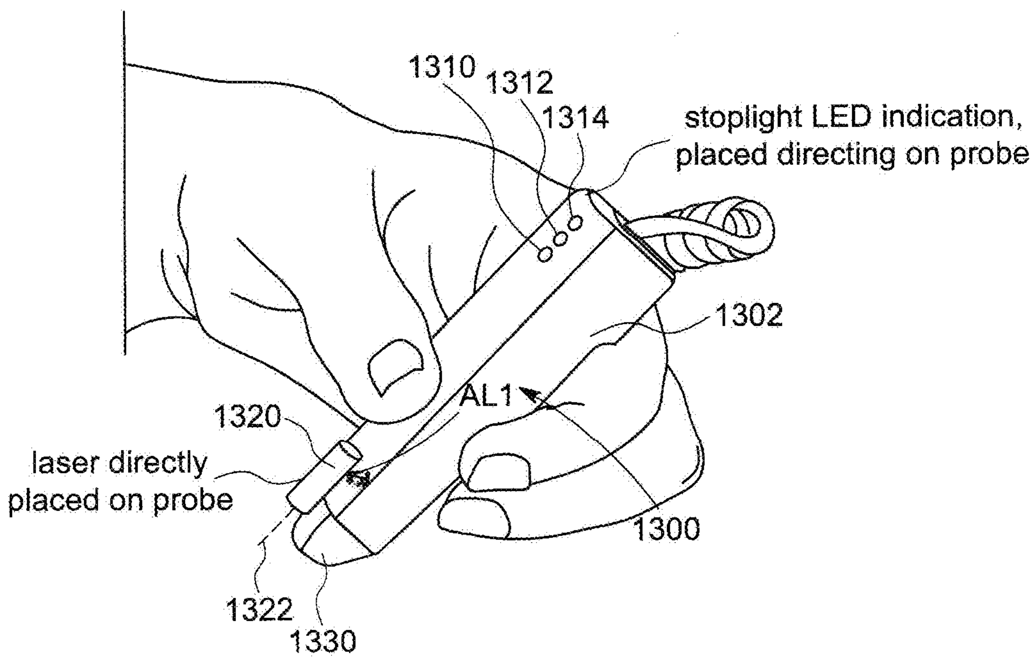
FIG. 13 is a perspective view of an artery location device in which the pointer and the LED array are located on the main body of the device according to an alternate embodiment.

With reference now to FIG. 13, another alternate implementation of the artery location device 1300 includes a housing/main body 1302 that omits the overlying arm described above. The indicator (e.g.) discrete LEDs 1310, 1312 and 1314 are located directly on the proximal end of the main body 1302. In this embodiment, there are three LEDs, that can each define a discrete color—for example red (1310), yellow (1312) and green (1314), in the form of a stoplight, in which red indicates no or minimal blood flow, yellow indicates some blood flow and green indicates significant blood flow detected. In this exemplary embodiment, the pointer assembly 1320 is located at the distal end of the main body 1302, and is angled (angle AL1) relative to the body elongation direction to direct a spot 1322 slightly ahead of the Doppler probe tip 1330.

Figure 14:
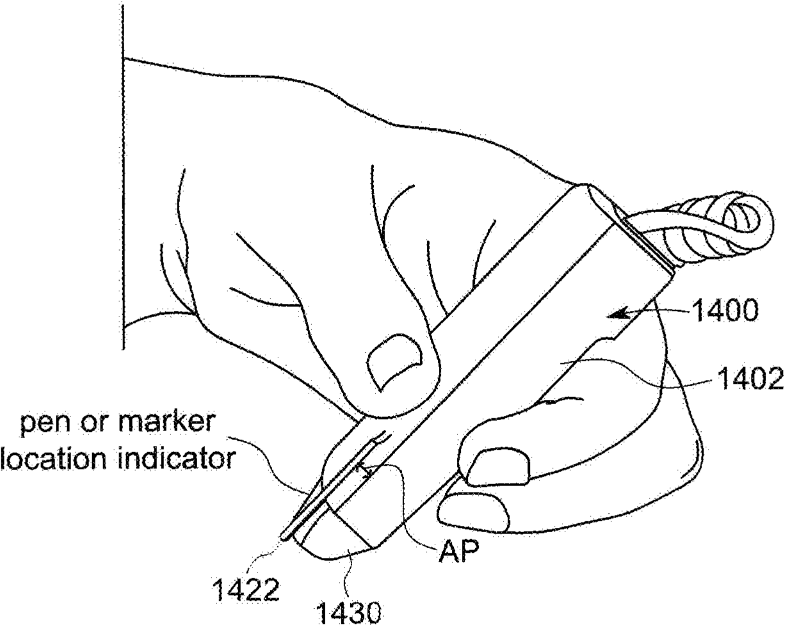
FIG. 14 is a perspective view of an artery location device in which a pen or physical pointer, mounted along the main body of the device, is employed to indicate artery location according to an alternate embodiment.

With reference now to FIG. 14, another alternate implementation of the artery location device 1400 includes a housing/main body 1402 that, again, omits the overlying arm described above. This version can include an appropriate indicator (not shown) that assists the user in localizing the artery. The artery can also be localized (e.g. in part) by use of an audible signal—for example, a periodic beep or changing frequency. The localization indicator is interconnected to the processing platform and operates in accordance with the procedure above. In this exemplary embodiment, the distal end of the main body includes a marking device 1420, such as a pen or other physical marker that is angled downwardly (angle AP) relative to the body elongation direction to allow the pen tip 1422 to be proximate the skin surface. In this manner as slight upward tip of the body causes the pen to leave a mark on the skin once the artery is located.

Figure 15:
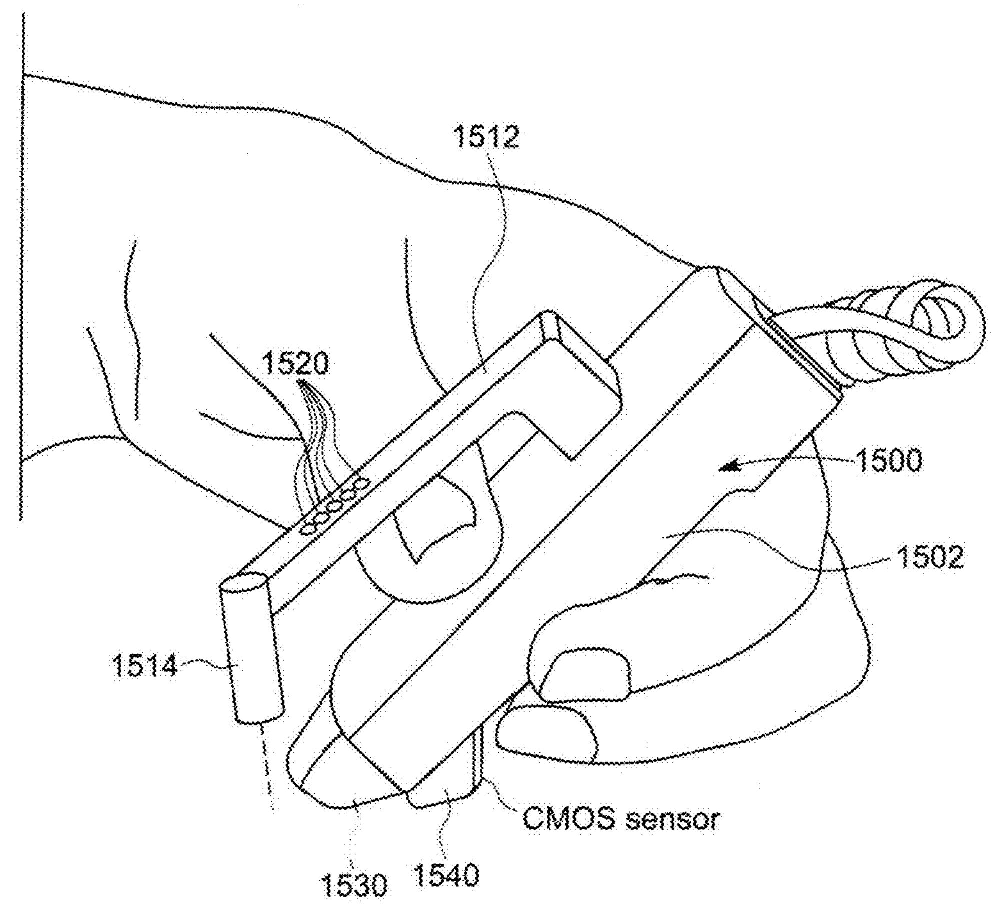
FIG. 15 is a perspective view of an artery location device in which an exemplary CMOS sensor is used to detect and quantify motion according to an alternate embodiment.

With reference now to FIG. 15, a further alternate implementation of the artery location device 1500 includes an overlying arm 1512, suspended over the main body 1502, with a distal laser pointer 1514 and indicator (e.g.) LEDs 1520. The function and structure of the components and processor are largely similar to those described in the above embodiments. This exemplary implementation omits an accelerometer, and instead, employs a conventional, commercially available CMOS sensor 1540 to detect device motion with respect to the patient. The sensor is interconnected with an appropriate input of the processor, which interprets the motion signals using known techniques. The CMOS sensor is housed in an appropriate base that maintains it in proximity to the Doppler probe tip 1530, while allowing both the probe tip and CMOS sensor to remain in contact with the patient at a proper tilt angle.

It is expressly contemplated that features of any of the alternate implementations described above can be combined with each other, or with features of other embodiments herein, in a manner clear to those of skill in the art.

VI Conclusion

It should be clear that the above-described artery location device, system, and method for operation/use thereof, provides the user with a straightforward, reliable and accurate mechanism for locating peripheral arteries that facilitates insertion of A-lines, and performing other medical procedures. The device can employ existing Doppler ultrasound technology and can be implemented as an add-on housing and processor using an existing probe or in a standalone device. A variety of indicators and marking mechanisms can be incorporated into the device to assist the user in pinpointing an artery.

The foregoing has been a detailed description of illustrative embodiments of the invention. Various modifications and additions can be made without departing from the spirit and scope of this invention. As discussed above, features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, as used herein, the terms "process" and/or "processor" should be taken broadly to include a variety of electronic hardware and/or software based functions and components (and can alternatively be termed functional "modules" or "elements"). Moreover, a depicted process or processor can be combined with other processes and/or processors or divided into various sub-processes or processors. Such sub-processes and/or sub-processors can be variously combined according to embodiments herein. Likewise, it is expressly contemplated that any function, process and/or processor herein can be implemented using electronic hardware, software consisting of a non-transitory computer-readable medium of program instructions, or a combination of hardware and software. Additionally, as used herein various directional and dispositional terms such as "vertical", "horizontal", "up", "down", "bottom", "top", "side", "front", "rear", "left", "right", and the like, are used only as relative conventions and not as absolute directions/dispositions with respect to a fixed coordinate space, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances of the system (e.g. 1-5 percent). Accordingly, this description is meant to be taken only by way of example, and not to otherwise limit the scope of this invention.

What is claimed is:

1. A location device for finding a peripheral artery with respect to a body based upon ultrasound signals from a Doppler ultrasound probe having a tip adapted to transmit and receive the ultrasound signals, comprising:

a processor that receives the ultrasound signals and processes the ultrasound signals to recognize blood flow of the peripheral artery, the processor quantifying the recognized blood flow based upon signal strength; and a housing having (a) a visual indicator, responsive to the processor, that displays an indication when the signal strength exceeds a predetermined threshold, and (b) a pointer, positioned adjacent to the tip, that pinpoints a location on the body beneath which the peripheral artery is located, wherein the pointer comprises a structured light source projecting a beam, and wherein the pointer is adapted to deactivate when movement sensed by an accelerometer exceeds the predetermined threshold.

2. The location device as set forth in claim 1, wherein the accelerometer is included in the housing, and wherein the accelerometer is interconnected with the processor, and the processor is adapted to provide a signal relative to at least one of the visual indicator and the pointer when movement sensed by the accelerometer exceeds a predetermined threshold.

3. The location device as set forth in claim 2, wherein the pointer and the visual indicator are located on an arm overlying an elongated main body of the housing.

4. The location device as set forth in claim 3, wherein the visual indicator comprises an array of a plurality of light sources located on the arm, and each of the plurality of light sources constructed and arranged to illuminate based upon the signal strength.

5. The location device as set forth in claim 4, wherein the plurality of light sources are LEDs that all have the same illumination color, or at least one of the LEDs has a differing illumination color from others of the LEDs so as to define differing threshold conditions, respectively.

6. The location device as set forth in claim 4, wherein the beam is activated when the signal strength exceeds a predetermined threshold.

7. The location device as set forth in claim 4, wherein the visual indicator comprises a display screen constructed and arranged to display information relative to the signal strength.

8. The location device as set forth in claim 1, wherein the ultrasound signals are passed through a bandpass filter, audio transformer and analog-to-digital converter.

9. The location device as set forth in claim 8, wherein the processor is constructed and arranged to identify heartbeat characteristics from filtered and digitized versions of the ultrasound signals and measure an intensity thereof.

10. A method for locating the peripheral artery by moving a location device of claim 1 with respect to a region of interest on the body of the patient based at least upon information provided by the visual indicator.

11. The method as set forth in claim 10, further comprising, inserting an A-line catheter into the peripheral artery at the pinpointed location.

12. The method as set forth in claim 10, further comprising, projecting the beam with the pointer.

13. The method as set forth in claim 12, further comprising, receiving, by the processor, data from the accelerometer, and providing therefrom, a signal relative to at least one of the visual indicator and the pointer when movement sensed by the accelerometer exceeds a predetermined threshold.

14. The method as set forth in claim 12, further comprising, deactivating the pointer when movement sensed by the accelerometer exceeds the predetermined threshold.

15. The method as set forth in claim 10, wherein the visual indicator comprises a display screen constructed and arranged to display information relative to the signal strength.

16. The method as set forth in claim 10, further comprising, passing the ultrasound signals through a bandpass filter, audio transformer and analog-to-digital converter.

17. The method as set forth in claim 16, further comprising, identifying heartbeat characteristics from filtered and digitized versions of the ultrasound signals and measuring an intensity thereof.

18. The location device as set forth in claim 8, wherein the processor is configured to determine a maximum signal strength over a sampled interval and activate the visual indicator proportionally thereto.

19. The location device as set forth in claim 1, wherein the structured light source projects a non-point pattern selected from a cruciform, reticle, or concentric pattern.

20. The location device as set forth in claim 1, wherein the pointer is configured to deactivate when the accelerometer detects motion exceeding a predetermined threshold to prevent misalignment of the pinpointed location.

* * * * *